United States Patent [19]

Sugio et al.

[11] 4,125,540

[45] Nov. 14, 1978

[54] PROCESS FOR STABILIZING TRIOXANE

[75] Inventors: Akitoshi Sugio, Ohmiya; Mutsuhiko Takeda, Matsudo; Makoto Mizutani; Takeo Suzumori, both of Tokyo, all of Japan

[73] Assignee: Mitsubishi Gas Chemical Company, Inc., Tokyo, Japan

[21] Appl. No.: 873,512

[22] Filed: Jan. 30, 1978

[30] Foreign Application Priority Data

Feb. 17, 1977 [JP] Japan ................................. 52-16389

[51] Int. Cl.$^2$ ............................................ C07D 323/06
[52] U.S. Cl. ................................................... 260/340
[58] Field of Search ............................................ 260/340

Primary Examiner—Norma S. Milestone
Attorney, Agent, or Firm—Flynn & Frishauf

[57] ABSTRACT

A process for stabilizing trioxane, characterized by adding thereto a specific trivalent organic phosphorus compound is disclosed.

8 Claims, No Drawings

PROCESS FOR STABILIZING TRIOXANE

BACKGROUND OF THE INVENTION

This invention relates to a process for stabilizing trioxane, and particularly relates to a process for preserving trioxane without causing oxidation and decomposition of trioxane.

Trioxane is a cyclic trimer of formaldehyde and is used as a raw material for producing oxymethylene polymer or copolymer and for producing industrial chemicals and is an important material from an industrial point of view. However, trioxane is unstable in the presence of oxygen and particularly so when in a melted state. The presence of even a slight amount of oxygen will oxidize and decompose melted trioxane to form formic acid and formaldehyde. Furthermore, when melted trioxane is solidified by cooling, it is known that, due to the presence of a small amount of impurities, a portion of the trioxane is polymerized to form polyoxymethylene. The trioxane used as a raw material for producing oxymethylene polymer or copolymer must be of high purity, the proportion of impurities, such as formic acid and formaldehyde, being very low or nil. Particularly, it is necessary that the formic acid content of the trioxane be less than 20 ppm.

Many prior art attempts have been made to preserve trioxane. Theoretically, oxidation and decomposition of trioxane can be prevented by preserving it in the absence of oxygen, but it is difficult to replace oxygen in the atmosphere, in which trioxane is placed, by an inert gas free from oxygen. It is known that addition of phenolic antioxidants or disulfides to trioxane will preserve it. However, though phenolic antioxidant is effective for preventing the formation of formic acid, it has little effect for preventing the formation of polyoxymethylene in case of solidifying trioxane by cooling it.

When trioxane is solidified by cooling it, the amount of polyoxymethylene formed is as high as several percent on the basis of weight of trioxane. When trioxane having such a high content of polyoxymethylene is melted again, the polyoxymethylene is precipitated in a white cotton-like state or white membrane state. This precipitate adheres to the inner surface of the pump, pipe or tank for storage. This results in clogging of the pipe, etc. and hinders the operation of the apparatus.

SUMMARY OF THE INVENTION

The present inventors have carried out research on a process for preserving trioxane without causing oxidation and decomposition of trioxane, or a process for preventing the formation of polyoxymethylene. As a result, it was found that trioxane can be preserved in a good state by adding thereto a specific trivalent organic phosphorus compound.

This invention relates to a process for stabilizing trioxane, characterized by adding to the trioxane at least one trivalent organic phosphorus compound selected from the group consisting of (a) compounds corresponding to the formula

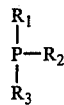

wherein $R_1$, $R_2$ and $R_3$ are the same or different and independently selected from the group consisting of an alkyl group having 1 to 18, preferably 1 to 10 carbon atoms, an aryl group having 6 to 18, preferably 6 to 10 carbon atoms, an aralkyl group having 7 to 18, preferably 7 to 10 carbon atoms, a cycloalkyl group having 3 to 18, preferably 5 to 6 carbon atoms, an alkoxy group having 1 to 18, preferably 1 to 10 carbon atoms, an aryloxy group having 6 to 18, preferably 6 to 10 carbon atoms, an aralkyloxy group having 7 to 18, preferably 7 to 10 carbon atoms, and a cycloalkyloxy group having 3 to 18, preferably 5 to 6 carbon atoms, or two of three R groups taken together represent an alkylene group having 4 to 6, preferably 4 to 5 carbon atoms, (b) compounds corresponding to the formula

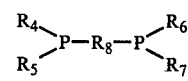

wherein $R_4$, $R_5$, $R_6$ and $R_7$ are the same or different and are independently selected from the group consisting of an alkyl group having 1 to 18, preferably 1 to 10 carbon atoms, an aryl group having 6 to 18, preferably 6 to 10 carbon atoms, an aralkyl group having 7 to 18, preferably 7 to 10 carbon atoms, a cycloalkyl group having 3 to 18, preferably 5 to 6 carbon atoms, and $R_4$ and $R_5$ taken together may represent an alkylene group having 4 to 6 carbon atoms, and $R_6$ and $R_7$ taken together may represent an alkylene group having 4 to 6 carbon atoms, and $R_8$ is an alkylene group having 1 to 6 carbon atoms in an amount sufficient to stabilize trioxane. The trivalent organic phosphorus compound selected from compounds corresponding to the formula

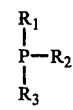

wherein $R_1$, $R_2$ and $R_3$ are the same or different and are independently selected from the group consisting of an alkyl group having 1 to 10 carbon atoms, an aryl group having 6 to 10 carbon atoms, an aralkyl group having 7 to 10 carbon atoms and a cycloalkyl group having 5 to 6 carbon atoms is more preferred.

DETAILED DESCRIPTION OF THE INVENTION

Examples of the trivalent organic phosphorus compounds include phosphines such as ethyltetramethylenephosphine, n-butyldimethylphosphine, triethylphosphine, ethylpentamethylenephosphine, dimethylphenylphosphine, methylethyl-n-pentylphosphine, diethyl-n-butylphosphine, tri-n-butylphosphine, methyldiphenylphosphine, ethyl-n-pentylphenylphosphine, methylbenzylphenylphosphine, ethyldiphenylphosphine, ethyl-n-hexylphenylphosphine, benzyl-n-butyl-n-propylphosphine, ethyldicyclohexylphosphine, isopropyldiphenylphosphine, ethylbenzylphenylphosphine, dibenzylethylphosphine, n-butyldiphenylphosphine, n-propylbenzylphenylphosphine, n-butylbenzylphenylphosphine, triphenylphosphine, cyclohexyldiphenylphosphine, dibenzyl-n-butylphosphine, dicyclohexylphenylphosphine, tricyclohexylphosphine, diphenylbenzylphosphine, dibenzylphenylphosphine, tri-p-tolylphosphine and tribenzylphosphine; phosphinites such as ethyl dipropylphosphinite, ethyl butylethylphosphinite, ethyl methylphenylphosphinite, ethyl ethylphenylphosphinite, ethyl dibutylphosphinite, methyl diphenylphosphinite, ethyl diphenylphosphinite, phenyl diphenylphosphinite, and phenyl dibenzylphosphinite; phosphonites such as dimethyl ethylphosphonite, diethyl ethylphosphonite, diphenyl ethylphosphonite, diethyl propylphosphonite, diethyl butylphosphonite, diethyl phenylphosphonite, dimethyl phenylphosphonite and diethyl benzylphosphonite; triesters of phosphorous acid such as trimethyl phosphite, triethyl phosphite, tri-n-propyl phosphite, tri-iso-propyl phosphite, tri-n-butyl phosphite, triphenyl phosphite, tricyclohexyl phosphite, tribenzyl phosphite, tritolyl phosphite, tri-3-naphthyl phosphite, tridecyl phosphite and trinonylphenyl phosphite; and diphosphines such as 1.5-bis(diethylphosphino)pentane, 1.4-bis(dicyclohexylphosphino)butane, 1.5-bis(dicyclohexylphosphino)pentane, bis(diphenylphosphino)methane, 1.2-bis(diphenylphosphino)ethane, 1.2-bis(ethylphenylphosphino)ethane, 1.4-bis(ethylphenylphosphino)butane and 1.6-bis(cyclohexylphenylphosphino)hexane. Triphenylphosphine, tri-p-tolylphosphine and tri-n-butylphosphine are most preferred.

The amount of the trivalent organic phosphorous compound added to the trioxane depends on the amount of impurities in the trioxane, the oxygen content in the atmosphere in which the trioxane is placed and the kind of phosphorus compounds employed, so the amount of the trivalent organic phosphorus compound added is not critical. Generally, the amount may be about 10– about 1000 1000 ppm, preferably about 20– about 500 ppm on the basis of weight of trioxane.

According to the present invention, trioxane can be preserved in a good state for at least 3 days even under severe conditions, such as melted state in air. After storage of trioxane containing the phosphorus compound, little or no formic acid and formaldehyde are formed.

Usually after melted trioxane containing the phosphorus compound is preserved, solidified and melted again, precipitaate of polyoxymethylene is not formed, but if polyoxymethylene is formed, the amount formed is very small.

When a portion of the oxygen in the atmosphere in which trioxane is placed is replaced by nitrogen or argon or when trioxane is preserved in solid state, trioxane can be preserved for a long time by adding thereto a small amount of the phosphorus compound.

Trioxane containing the phosphorus compound can be used for the polymerization reaction as it is. In other words trioxane containing the phosphorus compound can be used for the polymerization reaction in the presence of, for example, a boron trifluoride catalyst or its complex catalyst, whereby polyoxymethylene having high molecular weight can be obtained in a high yield. However, when trioxane containing the phosphorus compound is polymerized, a somewhat large amount of catalyst is necessary. As occasion demands, the trivalent organic phosphorus compound may be removed from trioxane through distillation or the like, before polymerizing the trioxane.

This invention is further illustrated, but in no way limited, by the following Examples. The parts and percentages are by weight unless otherwise specified.

EXAMPLE 1

To 500 grs of melted trioxane containing 2 ppm of formic acid and 1 ppm of formaldehyde as impurities was added 58.2 ppm of triphenylphosphine. The resulting mixture was placed in an Erlenmeyer flask. The flask was closed and was maintained at 65° C.–75° C. After three days, the formic acid content and formaldehyde content in the trioxane were 4 ppm and 3 ppm, respectively. In this case, even when trioxane was maintained in melted state, the formation of formic acid and formaldehyde was very small. 100 grs of the trioxane containing the phosphorus compound was solidified by cooling it and was melted by heating it again. The polyoxymethylene formed during the above operation was filtered and washed with acetone. The precipitate weighed 3.2 mg.

250 grs of the trioxane which had been preserved for three days as mentioned above was placed in portable kneader having two sigma-blades and 25 grs of cyclohexane and 6.3 grs of ethylene oxide were added thereto, and the resulting mixture was maintained at 65° C. When 125 seconds passed after boron trifluoride etherate in amount of 0.18 milli mole per mole of trioxane had been added to the mixture as a catalyst, the mixture turned whitish. On continuing the polymerization for one hour, the polymerization was terminated. The resulting polymer was removed therefrom and was dried. The yield of the polymer was 92%. The intrinsic viscosity of the polymer was 1.59 dl/g, measured at 60° C. in p-chlorophenol containing 2% alpha-pinene.

EXAMPLES 2–9

According to the procedure of Example 1, each of the trivalent organic phosphorus compounds as given in Table 1 was added to melted trioxane, and then the trioxane containing each of the phosphorus compounds was maintained at 65° C.–75° C. for 3 days. The amount each of formic acid and formaldehyde was measured.

100 grs of the trioxane containing the phosphorus compound was solidified and melted again as in Example 1. The polyoxymethylene formed was measured. The results are shown in Table 1.

COMPARATIVE EXAMPLE 1

The procedure of Examples 2–9 was repeated except that no trivalent organic phosphorus compound was added to trioxane. The results are shown in Table 1.

Table 1

| Example No. | Example 2 | Example 3 | Example 4 | Example 5 | Example 6 | Example 7 | Example 8 | Example 9 | Comparative Example 1 |
|---|---|---|---|---|---|---|---|---|---|
| Trivalent organic phosphorus compound | triphenyl phosphine | triphenyl phosphine | tri-n-butyl phosphine | triphenyl phosphite | ethyl diphenyl-phosphinite | diethyl phenyl-phosphonite | 1,2-bis-(diphenyl-phosphino)-ethane | tri-p-tolyl-phosphine | — |
| Amount of phosphorus compound added | 29.1 ppm | 291 ppm | 225 ppm | 334 ppm | 288 ppm | 450 ppm | 290 ppm | 48 ppm | — |
| Amount of formic acid formed after the trioxane | | | | | | | | | |

Table 1-continued

| Example No. | Example 2 | Example 3 | Example 4 | Example 5 | Example 6 | Example 7 | Example 8 | Example 9 | Comparative Example 1 |
|---|---|---|---|---|---|---|---|---|---|
| was maintained at 65 – 75° C for three days | 3 ppm | 10 ppm | 5 ppm | 4 ppm | 6 ppm | 8 ppm | 9 ppm | 9 ppm | 131 ppm |
| Amount of formaldehyde formed after the trioxane was maintained at 65 – 75° C for three days | 2 ppm | 17 ppm | 2 ppm | 3 ppm | 9 ppm | 5 ppm | 13 ppm | 13 ppm | 44 ppm |
| Amount of white precipitate formed after the melted trioxane was solidified and melted again (per 100 grs of trioxane) | 3.0 mg | 3.0 mg | 1.4 mg | 860 mg | 125 mg | 320 mg | 15 mg | 2.5 mg | 1020 mg |

What is claimed is:

1. A process for stabilizing trioxane, trioxane, characterized by adding to the trioxane at least one trivalent organic phosphorus compound selected from the group consisting of (a) compounds corresponding to the formula $$\begin{array}{c} R_1 \\ | \\ P-R_2 \\ | \\ R_3 \end{array}$$

wherein $R_1$, $R_2$ and $R_3$ are the same or different and are independently selected from the group consisting of an alkyl group having 1 to 18 carbon atoms, an aryl group having 6 to 18 carbon atoms, an aralkyl group having 7 to 18 carbon atoms, a cycloalkyl group having 3 to 18 carbon atoms, an alkoxy group having 1 to 18 carbon atoms, an aryloxy group having 6 to 18 carbon atoms, a cycloalkyloxy group having 3 to 18 carbon atoms, and an aralkyloxy group having 7 to 18 carbon atoms, or two of three R groups taken together represent an alkylene group having 4 to 6 carbon atoms, and (b) compounds corresponding to the formula $$\begin{array}{c} R_4 \\ \phantom{R}\diagdown \\ \phantom{R_4R_5}P-R_8-P \\ \phantom{R}\diagup \phantom{RRRRRR}\diagdown \\ R_5 \phantom{RRRRRRRR} R_7 \end{array} \begin{array}{c} R_6 \\ \\ \\ \\ R_7 \end{array}$$

wherein $R_4$, $R_5$, $R_6$ and $R_7$ are the same or different, and are independently selected from the group consisting of an alkyl group having 1 to 18 carbon atoms, an aryl group having 6 to 18 carbon atoms, an aralkyl group having 7 to 18 carbon atoms, a cycloalkyl group having 3 to 18 carbon atoms, and $R_4$ and $R_5$ taken together may represent an alkylene group having 4 to 6 carbon atoms and $R_6$ and $R_7$ taken together may represent an alkylene group having 4 to 6 carbon atoms, and $R_8$ is an alkylene group 1 to 6 carbon atoms in an amount sufficient to stabilize trioxane.

2. The process as defined in claim 1 wherein the trivalent organic phosphorus compound is selected from compounds corresponding to the formula $$\begin{array}{c} R_1 \\ | \\ P-R_2 \\ | \\ R_3 \end{array}$$

wherein $R_1$, $R_2$ and $R_3$ are the same or different and are independently selected from the group consisting of an alkyl group having 1 to 10 carbon atoms, an aryl group having 6 to 10 carbon atoms, an aralkyl group having 7 to 10 carbon atoms, a cycloalkyl group having 5 to 6 carbon atoms, an alkyloxy group having 1 to 10 carbon atoms, an aryloxy group having 6 to 10 carbon atoms, an aralkyloxy group having 7 to 10 carbon atoms and a cycloalkyloxy group having 5 to 6 carbon atoms.

3. The process as defined in claim 1 wherein the trivalent organic phosphorus compound is selected from compounds corresponding to the formula $$\begin{array}{c} R_1 \\ | \\ P-R_2 \\ | \\ R_3 \end{array}$$

wherein $R_1$, $R_2$ and $R_3$ are the same or different and are independently selected from the group consisting of an alkyl group having 1 to 10 carbon atoms, an aryl group having 6 to 10 carbon atoms, an aralkyl group having 7 to 10 carbon atoms and a cycloalkyl group having 5 to 6 carbon atoms.

4. The process as defined in claim 1 wherein the trivalent organic phosphorus compound is triphenylphosphine.

5. The process as defined in claim 1 wherein the trivalent organic phosphorus compound is tri-p-tolylphosphine.

6. The process as defined in claim 1 wherein the trivalent organic phosphorus compound is tri-n-butylphosphine.

7. The process as defined in claim 1 wherein the amount of the trivalent organic phosphorus compound added ranges from about 10 ppm to about 1000 ppm on the basis of weight of the trioxane.

8. The process as defined in claim 1 wherein the amount of the trivalent organic phosphorus compound added ranges from about 20 ppm to about 500 ppm on the basis of weight of the trioxane.

* * * * *